(12) United States Patent
Schultz et al.

(10) Patent No.: US 9,145,574 B2
(45) Date of Patent: Sep. 29, 2015

(54) MATERIALS AND METHODS FOR ASSESSING AND MAPPING MICROBES AND MICROBIAL BIOFILMS ON WOUNDS

(75) Inventors: Gregory S. Schultz, Gainesville, FL (US); Priscilla Lorraine Phillips, Gainesville, FL (US); Edith Marion Sampson, Williston, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/131,920

(22) PCT Filed: Apr. 26, 2010

(86) PCT No.: PCT/US2010/032378
§ 371 (c)(1),
(2), (4) Date: Jul. 11, 2011

(87) PCT Pub. No.: WO2010/124277
PCT Pub. Date: Oct. 28, 2010

(65) Prior Publication Data
US 2012/0322048 A1  Dec. 20, 2012

Related U.S. Application Data

(60) Provisional application No. 61/172,534, filed on Apr. 24, 2009.

(51) Int. Cl.
C12Q 1/00 (2006.01)
C12Q 1/37 (2006.01)
A61K 49/00 (2006.01)
A61K 31/74 (2006.01)
A61L 15/16 (2006.01)
(Continued)

(52) U.S. Cl.
CPC ............. *C12Q 1/04* (2013.01); *G01N 33/569* (2013.01)

(58) Field of Classification Search
CPC ..... A61F 13/00; A61F 15/00; A61F 2013/00; A61B 5/00; A61B 2010/00; C09J 1/00; C09J 7/00; C09J 2201/00; C12M 1/00; C12Q 2304/00; G01N 1/00
USPC ........ 435/4, 243, 805, 7.32; 602/41, 903, 904
See application file for complete search history.

(56) References Cited

U.S. PATENT DOCUMENTS 5,912,114 A * 6/1999 Hutchinson et al. ............. 435/4
8,058,024 B2 * 11/2011 Schultz et al. ................. 435/23
(Continued)

FOREIGN PATENT DOCUMENTS

GB 2323166 A * 9/1998
WO WO 2009122188 A2 * 10/2009

OTHER PUBLICATIONS

Webster et al. 2006 (Distribution of bacterial proteins in biofilms formed by non-typeable Haemophilus influenza; Journal of Historchemistry & Cytochemistry; 54(7):829-842).*
(Continued)

*Primary Examiner* — Gary Nickol
*Assistant Examiner* — Mary Lyons
(74) *Attorney, Agent, or Firm* — Saliwanchik, Lloyd & Eisenschenk (57) ABSTRACT

The subject invention provides point-of-care assays for assessing the topographical distribution of microbial biofilm and/or specific microorganisms in wounds.

4 Claims, 11 Drawing Sheets
(4 of 11 Drawing Sheet(s) Filed in Color)

(51) Int. Cl.
*C12Q 1/04* (2006.01)
*G01N 33/569* (2006.01)

(56) References Cited

U.S. PATENT DOCUMENTS

2006/0030539 A1 2/2006 Nick et al.
2009/0258382 A1* 10/2009 Schultz et al. .................. 435/23

OTHER PUBLICATIONS

Boles et al. 2008 (agr-Mediated dispersal of *Staphylococcus aureus* biofilms; PLoS Pathogens, 4:1-13).*
Cuny et al. 1991 "Pocket Blotting": A Method for Transferring Nucleic Acids onto Nylon Membranes; Anyalyitcal biochemistry 192:1-5.*
Cabodi et al. 2007 (An active wound dressing for controlled convective mass transfer with the wound bed; J. Biomed. Mater. Res. B. Apll. Biomater. 82(1):210-22).*
Boyd et al. 1995 (*Pseudomonas aeruginosa* biofilms: role of alginate exopolysaccharide; J Ind Microb 15(3):162-168).*
Strathmann et al. 2001 (Application of fluorescently labelled lectins for the visualization and biochemical characterization of polysaccharides in biofilms of *Pseudomonas aeruginosa*; J of Microb. Meth. 50:237-248).*
Davis, S.C. et al., "Microscopic and physiologic evidence for biofilm-associated wound colonization in vivo," *Wound Repair and Regeneration,* 2008, pp. 23-29, vol. 16.
Dynes, J.J. et al., "Quantitative mapping of chlorhexidine in natural river biofilms," *Science of the Total Environment,* 2006, pp. 369-383, vol. 369.
James, G.A. et al., "Biofilms in chronic wounds," *Wound Repair and Regeneration,* 2008, pp. 37-44, vol. 16.
Leiknes, T. et al., "The development of a biofilm membrane bioreactor," *Desalination,* 2007, pp. 135-143, vol. 202.
Monroe, D., "Looking for chinks in the armor of bacterial biofilms," *PLoS Biology,* Nov. 2007, pp. 2458-2461, vol. 5, Issue 11.

\* cited by examiner

MATERIALS AND METHODS FOR ASSESSING AND MAPPING MICROBES AND MICROBIAL BIOFILMS ON WOUNDS

CROSS-REFERENCE TO A RELATED APPLICATION

This application is a National Stage Application of International Application Number PCT/US2010/032378, filed Apr. 26, 2010; which claims the benefit of U.S. provisional application Ser. No. 61/172,534, filed Apr. 24, 2009, which are incorporated herein by reference in their entirety.

BACKGROUND OF INVENTION

Bacterial biofilms are highly heterogeneous and found in the natural, industrial, and medical environments and include microorganisms embedded in a glycocalyx that is predominantly composed of microbially produced exopolysaccharide (Flemming et al., in "Biofilms: recent advances in their study and control", 2000, pp. 19-34, Harwood Academic Publishers, Amsterdam, The Netherlands; Costerton et al., Science, 1999, 284:1318-1322; Costerton et al., J. Bacteriol., 1994, 176:2137-2142; Keevil et al., Microbiol. Eur., 1995, 3:10-14). The glycocalyx can provide protection against environmental change, such as antimicrobial agents, and may act as a reservoir for nutrients and ions (Allison, Microbiol. Eur., 1993, Nov./Dec. 16-19; Mah et al., Trends Microbiol., 2001, 9:34-39; Stewart and Costerton, Lancet, 2001, 358:135-138).

The presence of persistent bacterial biofilms is known to contribute to the molecular pathologies of many diseases such as periodontal disease, cystic fibrosis, and chronic otitis media, as well as infections associated with contact lenses, urinary catheters, central venous catheters, endotracheal tubes, and surgical devices (R. M. Donlan and J. W. Costerton, Clin. Microbiol. Rev. 15, 167-193 (2002); J. W. Costerton, P. S. Stewart, E. P. Greenberg, Science 284, 1318-1322 (1999)). There has been increased recognition that bacterial colonization, particularly the presence of microbial biofilm, is one of the main factors causing delayed wound healing (S. G. Jones, R. Edwards, D. W. Thomas, Int. J. Low Extrem. Wounds 3, 201-208 (2004); Edwards, R., Harding K G (2004) "Bacteria and Wound Healing" Curr Opin Infect Dis 17:91-96; and James, G A, Swogger, E. Wolcott R, Pulcini E., Secor P., Sestrich, J. Costerton, J. W., Stewart, P. S. (2008) "Biofilms in Chronic Wounds" Wound Repair Regen 16:37-44). Recent investigations indicate that most chronic skin wounds (~60%) contain bacterial biofilms and a small percentage of acute wounds (6%) clearly have bacterial biofilms (James et al., 2008, ibid.).

Bacteria embedded in biofilms are physiologically different from planktonic (free-floating) ones. Regardless of location or diversity, all microbial biofilms have a common developmental process including attachment, colonization, maturation, and dispersion (R. M. Donlan and J. W. Costerton, Clin. Microbiol. Rev. 15, 167-193 (2002); J. W. Costerton, P. S. Stewart, E. P. Greenberg, Science 284, 1318-1322 (1999); M. E. Davey and G. A. O'Toole, Microbiol. Mol. Biol. Rev. 64, 847-867 (2000); A. L. Spoering and M. S. Gilmore, Curr. Opin. Microbiol. 9, 133-137 (2006); and P. Hunter, EMBO Rep. 9, 314-317 (2008)). Planktonic bacteria reversibly adhere to surfaces, such as open wounds or medical devices, and/or coaggregate (specific bacterial cell-to cell attachment) at surface interfaces (air-water). In response to environmental signals, they become sessile (irreversibly attached) and secrete a protective matrix consisting of self-synthesized extracellular polymeric substance (EPS), then differentiate and form microcolonies, and finally build up to form complex three dimensional biofilms (J. W. Costerton, P. S. Stewart, E. P. Greenberg, Science 284, 1318-1322 (1999); D. G. Davies et al., Science 280, 295-298 (1998); P. Gilbert, J. Das, I. Foley, Adv. Dent. Res. 11, 160-167 (1997); and R. M. Donlan and J. W. Costerton, Clin. Microbiol. Rev. 15, 167-193 (2002)).

The structural complexity of biofilms is thought to be analogous to tissues of higher organisms. Biofilm structures consist of interstitial channels and distinctly located subpopulations of cells with different patterns of gene expression (P. Watnick and R. Kolter, J. Bacteriol. 182, 2675-2679 (2000)). These structural features are believed to allow the dense cell populations in biofilms to overcome the potential limitation of nutrients and oxygen, enable exchange of metabolic products and signal molecules, and facilitate removal of toxic metabolic products and waste (K. D. Xu, P. S. Stewart, F. Xia, C. T. Huang, G. A. McFeters, Appl. Environ. Microbiol. 64, 4035-4039 (1998); M. R. Parsek and E. P. Greenberg, Trends Microbiol. 13, 27-33 (2005); D. de Beer, P. Stoodley, Z. Lewandowski, Biotechnology and Bioengineering 44, 636-641 (2004); D. de Beer, P. Stoodley, F. Roe, Z. Lewandowski, Biotechnology and Bioengineering 43, 1131-1138 (2004); J. W. Costerton, Z. Lewandowski, D. E. Caldwell, D. R. Korber, H. M. Lappin-Scott, Annu. Rev. Microbiol. 49, 711-745 (1995); and P. Stoodley, D. Debeer, Z. Lewandowski, Appl. Environ. Microbiol. 60, 2711-2716 (1994)).

Compared to planktonic bacteria, coaggregated surface attached (sessile) microcolonies of bacteria in biofilms such as those found in chronic skin wounds have enhanced resistance to killing by endogenous antibodies and phagocytic cells, as well as by exogenous antibiotics, antiseptics, and disinfectants (J. W. Costerton, P. S. Stewart, E. P. Greenberg, Science 284, 1318-1322 (1999); R. M. Donlan and J. W. Costerton, Clin. Microbiol. Rev. 15, 167-193 (2002); R. Edwards and K. G. Harding, Curr. Opin. Infect. Dis. 17, 91-96 (2004); and J. G. Leid et al., J. Immunol. 175, 7512-7518 (2005)). This has lead to the more recent appreciation of the need for reassessing the efficacy of conventional antimicrobial treatments and the need to develop new treatment strategies specific for managing microbial biofilm in wounds, particularly in chronic wounds.

Chronic wounds recalcitrant to healing are an increasingly grave worldwide problem. They include diabetic foot ulcers (DFU), pressure ulcers (PU), and venous leg ulcers (VLU), which lead patients to chronic pain, impaired mobility, frequent amputations, and reduced life quality. More than 1% of the population in developed countries has been estimated to experience a chronic wound during their lifetime, an occurrence that is increasing with the number of lifestyle diseases such as obesity, diabetes, and cardiovascular diseases (F. Gottrup, M. S. Agren, T. Karlsmark, Wound Repair Regen. 8, 83-96 (2000)). In 2000, diabetes was estimated to affect 171 million people worldwide and is predicted to more than double by 2030 (G. A. Matricali, G. Dereymaeker, E. Muls, M. Flour, C. Mathieu, Diabetes Metab Res. Rev. 23, 339-347 (2007)). Approximately 15% of diabetic patients will develop lower extremity ulcers and 14-24% of DFU will eventually undergo amputation (G. E. Reiber, Diabet. Med. 13 Suppl 1, S6-11 (1996); and G. E. Reiber et al., Diabetes Care 22, 157-162 (1999)). 1% of the world's population suffer with VLU (J. T. Trent, A. Falabella, W. H. Eaglstein, R. S. Kirsner, Ostomy Wound Manage. 51, 38-54 (2005)).

The expenditure on chronic wounds is enormous and a financial toll worldwide. In 2004, the total cost of DFU rose to $10 billion, including direct expenses (about 4% of the total personal health spending) and another $5 billion in indirect expenses (disability, nursing homes, etc.). The majority of the direct cost of DFU (71-88%) is attributed to in-hospital stay (length of stay being the most important factor) while the single contribution of other factors (drugs, investigations, surgery, orthopedic appliances, visits to foot care specialists, home care) is comparatively low (>10%) (G. A. Matricali, G. Dereymaeker, E. Muls, M. Flour, C. Mathieu, *Diabetes Metab Res. Rev.* 23, 339-347 (2007)). Medicare reimbursement remains insufficient, with hospital costs exceeding reimbursement by almost $7500 per patient (Matricali et al., 2007, ibid.).

The center of disease control (CDC) estimates that among all nosocomial infections, biofilm-based infections contribute more than 65% (C. Potera, *Science* 283, 1837-+ (1999)) which has lead to an increase in patients' hospitalization by 2 to 3 days and additional costs of over $1 billion per year (L. K. Archibald and R. P. Gaynes, *Infect. Dis. Clin. North Am.* 11, 245-255 (1997)). As mentioned previously, the presence of microbial biofilm is one of the main factors believed to cause delayed wound healing (R. Edwards and K. G. Harding, *Curr. Opin. Infect. Dis.* 17, 91-96 (2004); S. G. Jones, R. Edwards, D. W. Thomas, *Int. J. Low Extrem. Wounds* 3, 201-208 (2004); and G. A. James et al., *Wound. Repair Regen.* 16, 37-44 (2008)). In the U.S. alone, chronic wounds affect over 4 million people with treatment costs of $9 billion per year (K. Izadi and P. Ganchi, *Clin. Plast. Surg.* 32, 209-222 (2005)). As a consequence, chronic wound healing is of significant importance to human health as well as economic development.

Unfortunately, there are currently no topographical wound assessment devices for the detection of wound biofilm or microorganisms. In addition, there is a need for rapid point-of-care devices for detecting wound bacteria and/or bacterial biofilm. The conventional method of diagnosing the presence of microorganisms (bacterial and fungal) in wounds is technologically complex and time consuming, involving sampling, culturing, and typing in clinical microbiology labs. This procedure can cause significant delays in assessing the condition of the wound and administering appropriate treatment.

In addition to the delay in administering appropriate treatment to patients due to the time required analyzing samples, it has been well documented that biofilm in chronic wounds contain a number of uncultivable and difficult to culture species (P. G. Bowler and B. J. Davies, *Int. J. Dermatol.* 38, 573-578 (1999); C. E. Davies et al., *J. Clin. Microbiol.* 42, 3549-3557 (2004); and S. E. Dowd et al., *BMC. Microbiol.* 8, 43 (2008)), making the characterization of the wound microflora and identification of potential pathogens or primary contributors to pathology difficult. This basic deficiency in diagnosis often results in ineffective treatment strategies.

Thus, there is a need for a rapid, simple, inexpensive, point-of-care assay that would detect and localize bacterial biofilms and/or microorganism in chronic wounds in order to develop more effective treatment strategies in wound management.

BRIEF SUMMARY

The subject invention provides point-of-care methods for assessing the topographical distribution of microbial biofilm and/or specific microorganisms in wounds.

Biofilms are a major factor that contribute to poor healing of wounds. Advantageously, the topographical diagnostic materials and methods of the subject invention can be used to detect the presence and location of microbial biofilm, as well as microorganisms, on wounds.

Rapid, point-of-care detection of microbial biofilm and specific microorganisms (e.g., pathogenic species) that can be accomplished using the systems and methods of the invention enable more effective treatment guidelines/strategies in wound management. Such systems and methods assist health care workers (e.g., physicians) in assessing a wound for the presence and/or topographical distribution of microbial biofilm and/or specific microorganisms (class, genera, species etc.). The point-of-care biofilm and/or microbial wound assay of the subject invention facilitates designing personalized treatment strategies, as well as justifying the use of advanced and/or more costly wound management technologies that may be appropriate to promote wound healing on a case-by-case basis.

Furthermore, the data generated according to the subject invention can be readily archived. This data can be, for example, digital photography and the topographical data regarding a patient's wound. The storage and evaluation of this data facilitates long-term comparative assessment as well as the ability to track trends with respect to infection characteristics and treatment efficacy in managing microorganisms and/or microbial biofilm in the wound.

In a preferred embodiment, the topographical assay of the subject invention involves taking an impression of a wound and processing the impression in order to produce a two dimensional map of the location of microbial biofilm and/or specific microorganisms on the wound.

In further preferred embodiments of the subject invention, the primary targets used to indicate the general presence of microbial biofilm are components found in the extracellular matrix of microbial biofilm. There can be, for example, signal molecules, polyanionic bacterial exopolysaccharides such as poly-$\beta$-(1-6)-N-acetyl-D-glucosamine and alginic acid.

In addition to detecting and locating biofilm, the use of, for example, reporter-ligands to specific microbial markers (solely or in addition to reporter-ligands to general microbial biofilm extracellular matrix targets) allows the presence of specific microbial classes, genera, and/or species to be located on the biofilm wound map.

The detection ligand molecules can be, for example, monoclonal or polyclonal antibodies, DNA aptamers, protein aptamers, phage display, or any other macromolecular recognition technology. The reporter molecule can be fluorescent, chemiluminescent, chromogenic, or any other appropriate electromagnetic signal.

The appropriate method(s) of visual assessment and data recording of the biofilm wound map are correlated with the reporter molecule and assay membrane used in accordance with techniques well known to those skilled in the art.

In a second embodiment, the subject invention provides a very, simple, easy and quick wound map procedure wherein a high capacity blotting membrane is applied to a wound and then the membrane is contacted with dye molecules that selectively stain the biofilm matrix. In this embodiment the membrane does not contain antibodies (or other specific binding agents) to the biofilm components. Instead, the membrane binds, for example, proteins, polysaccharides, and DNA in a non-selective manner. The polyanionic polysaccharide matrix of the biofilm is then detected by staining with polycationic dye molecules. The dye may be, for example, alcian blue or ruthenium red.

In a third embodiment, for wounds in which a topographical map assay device would be impractical or unfeasible, a point-of-care bacteria and bacterial biofilm wound assay using a single sampling platform, such as a swab, is provided. Such a device would be amenable for assessment of targets other that outer dermal wounds (i.e. eye, ear, etc).

By using the assays of the subject invention, health care workers can assess a wound for the presence and topographical distribution of microbial biofilm and/or specific microorganisms. This biofilm and/or microbial wound map aids in debridement strategies as well as in designing personalized treatment strategies. The results of the topographical distribution assay can also be used to provide justification for the use of advanced and/or more costly wound management technologies that may be appropriate to promote wound healing on a case-by-case basis.

The use of this device also facilitates assessment of the effect of various antimicrobial treatment strategies in managing microorganisms and/or microbial biofilm in the wound.

BRIEF DESCRIPTION OF DRAWINGS

The file of this patent contains at least one drawing executed in color. Copies of this patent with color drawings(s) will be provided by the Patent and Trademark Office upon request and payment of the necessary fee.

FIG. 1A-C shows a schematic of the topographical wound map assay of the subject invention.

FIG. 2A-H illustrates blots of the top ("wound bed") or bottom of porcine skin explants onto HYBOND™-N+ membrane and stained with 5 mg/ml Alcian Blue and washed with PBS. A) Blot of the bottom of an explant with 3 day mature PAO1 biofilm. B) Blot of the top of an explant with 3 day mature PAO1 biofilm. C) Second blot of the top of an explant with 3 day mature PAO1 biofilm after blotting on spot B. D) Blot of the top of an explant with 3 day mature PAO1 biofilm. E) Blot of the top of an explant with 1 day immature PAO1 biofilm. F) Blot of the bottom of an explant with 1 day immature PAO1 biofilm. G). Blot of the top of an unsterile explant (negative control). H) Blot of the bottom of an unsterile explant (negative control).

FIG. 3A-F illustrates blots of the top ("wound bed") or bottom of porcine explants onto HYBOND™-N+ membrane and stained with 5 mg/ml Ruthenium Red and washed with PBS. A) Blot of the bottom of an explant with 3 day mature PAO1 biofilm. B) Blot of the top of an explant with 3 day mature PAO1 biofilm. C) Second blot of the top of an explant with 3 day mature PAO1 biofilm after blotting on spot B. D) Blot of the top of an explant with 3 day mature PAO1 biofilm. E) Blot of the top of an explant with 1 day immature PAO1 biofilm. F). Blot of the top of an unsterile explant (negative control).

FIG. 5A-C illustrates dot blots of Alginic acid. A solution of 5 mg/ml Alginic acid was 2-fold serially diluted and 2 µl of each dilution was dotted onto HYBOND™-N+ membrane and stained with 5 mg/ml of Alcian Blue or Ruthedium Red. A) Stained dot blot washed with PBS with 5 ul/ml Tween-80. B) Stained dot blot washed with PBS with 0.1% SDS. C) Stained dot blot washed with 40% methanol with 10% acetic acid solution.

FIG. 6A-D illustrates a wound map of *Pseudomonas aeruginosa* biofilm on porcine skin explants. A) Blot of the top of a pig skin explant with one day immature *Pseudomonas aeruginosa* PAO1 biofilm. Negative controls include B) blot of the top of a sterilized porcine skin explant without a biofilm; C) blot of top of unsterilized porcine skin explant; and D) blot of bottom of unsterilized skin explant.

FIG. 8A-B illustrates microscopic cryosections of dye staining *Pseudomonas aeruginosa* biofilms on pig skin.

FIG. 10A-B illustrates immunodetection of *Pseudomonas aeruginosa* biofilm on porcine explant biofilm with fluorescent antibodies to polyalginic acid, where the cryosections were incubated with a 1:100 dilution of 1 mg/mL anti-alginate antibody in blocking buffer for two hours at 4° C. They were then rinsed with PBS w/0.1% Tween 20 and incubated for one hour with 1:1000 dilution fluorescent anti-human antibody, then rinsed again and visualized under a fluorescent microscope. A) is a dark field fluorescent microscopic image of cryosection of pig skin explant with mature *Pseudomonas aeruginosa* biofilm immunostained with antibody to polyalginic acid antibody. B) is bright field microscopic image of the same cryosection of A).

FIG. 12A-B illustrates wound map of *Pseudomonas aeruginosa* biofilm on porcine skin wounds. A) illustrates wound map twenty minutes after inoculating planktonic bacteria. B) illustrates wound map twenty-four hour after inoculating planktktonic bacteria.

DETAILED DISCLOSURE

Bacterial colonization, particularly the presence of microbial biofilm, is one of the primary factors that can cause delayed wound healing. Also, the increased resistance of biofilm to antimicrobial treatments, relative to planktonic organisms, has been well documented. Unfortunately, the need for reassessing the efficacy of current antimicrobial treatments and to develop new treatment strategies specific for managing microbial biofilm in wounds, particularly chronic wounds, has only recently become appreciated.

The subject invention provides point-of-care methods for assessing the topographical distribution of microbial biofilm and/or specific microorganisms. Advantageously, the assays of the subject invention can be used to identify the location of biofilm and/or microbes on a wound, as well as to provide information about the chemical and/or biological characteristics of the biofilm and microbes.

Microbial biofilm distribution on wounds is a dynamic condition. Knowing the topographical location within the wound of microbial biofilm and/or microorganisms enables the health care provider to make informed decisions on the appropriate treatment strategies to be applied to the wound in a specific localized manner. The point-of-care topographical biofilm wound map of the subject invention provides health care workers (e.g. physicians, nurses, and others) immediate information on the microbial condition of the wound, thereby assisting and justifying the choice of treatment methods employed to promote wound healing.

Furthermore, the technology of the subject invention is amenable to archiving (e.g. digital photography) of the topographical data in the patient's care record, thereby facilitating long term comparative assessment.

In a preferred embodiment, the topographical assay involves taking an impression of the wound and processing the impression in order to produce a two dimensional map of the location of microbial biofilm and/or specific microorganisms (class, genera, species etc.) on the wound. Thus, the use of this device can aid in, for example, chronic wound treatment.

The molecule(s) targeted for detection and/or measurement can be polysaccharides or glycoproteins that contribute to the formation of biofilms. The primary targets, used to indicate the general presence of microbial biofilm, are preferably components found in the extracellular matrix of microbial biofilm (e.g. polyanionic bacterial exopolysaccharides such as poly-$\beta$-(1-6)-N-acetyl-D-glucosamine, alginic acid, etc.).

The use of reporter-ligands to specific microbial markers (solely or in addition to reporter-ligands to general microbial biofilm extracellular matrix targets) allows the presence of specific microbial classes, genera, and/or species to be located on the biofilm wound map.

The detection ligand molecule(s) can be monoclonal or polyclonal antibodies, DNA aptamers, protein aptamers, phage display, or any other macromolecular recognition that currently exists or will exist. The reporter molecule(s) will be fluorescent, chemiluminescent, chromogenic, or any other detectable signal.

In one embodiment, the subject invention can be used to detect *Pseudomonas aeruginosa* biofilm on a skin wound using a cationic membrane that binds anions such as polyalginic acid that make up the majority of the biofilm exopolymeric matrix. After blotting the membrane onto the wound with the biofilm, the membrane can be stained with a cationic red dye molecule that binds to the biofilm matrix. Planktonic *P. aeruginosa* bacteria (single cells) on wounds that are blotted with the cationic membrane and stained do not retain any red dye. Thus, the method is specific for the biofilm exopolymeric matrix.

Assays can be developed for naked eye or quantitative assessment using well-established, relatively inexpensive technical and non-technical personnel.

The appropriate methods of visual assessment and data recording of the biofilm wound map can be correlated with the reporter molecules and assay membranes used. The physical embodiment of the topographical wound map microbial biofilm reporter assay device correlates with the optimal means of assessing the target molecules.

In a second embodiment, the subject invention provides a very, simple, easy and quick wound map procedure. In this embodiment the membrane does not contain antibodies to the biofilm components. Instead, the membrane binds, for example, proteins, polysaccharides, and DNA in a non-selective manner. The polyanionic polysaccharide matrix of the biofilm is then detected by staining with polycationic dye molecules. The dye may be, for example, alcian blue or ruthenium red.

In yet another embodiment, biomolecules are bound to a non-specific membrane but then specific ligands are used to identify target molecules that have bound to the membrane. The specific ligand, may be, for example, antibodies, aptamers, or other macromolecular recognition entities.

Figure 4:
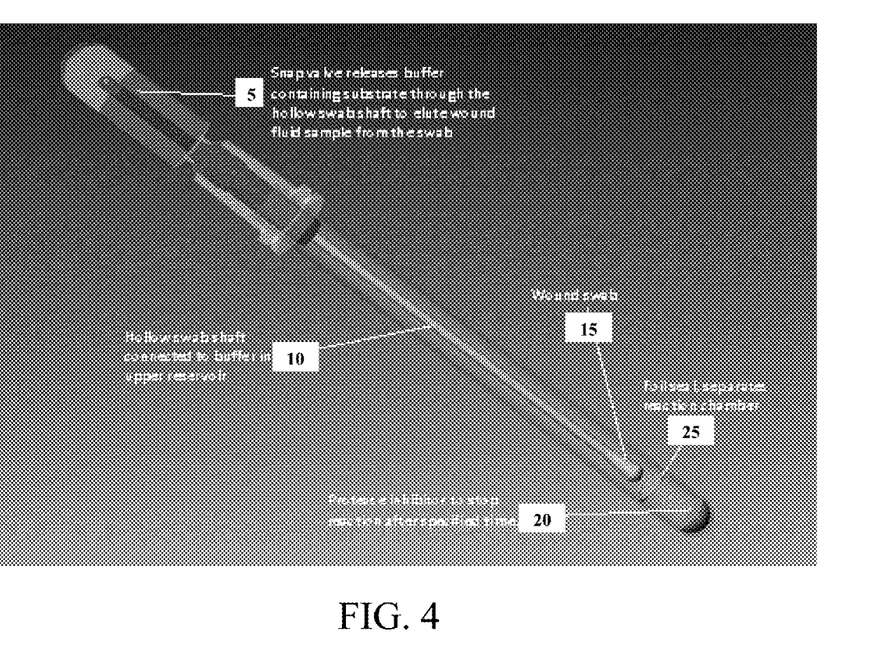
FIG. 4 illustrates an embodiment of a rapid, point of care matrix metalloproteinase (MMP) detector in accordance with the subject invention.

In a third embodiment, for wounds in which a topographical map assay device would be impractical or unfeasible, a point-of-care bacteria and bacterial biofilm wound assay using a single sampling platform, such as a swab, is provided. Such a device is amenable for assessment of targets other that outer dermal wounds (e.g. eye, ear, etc). FIG. 4 illustrates an example of a rapid, point-of-care sampling platform for indicating matrix metalloproteinase (MMP) detection. A movable wound swab 15 is provided for application to a wound to retrieve a sample. The swab 15 includes a hollow swab shaft 10 connected to buffer in an upper reservoir. A snap valve 5 releases the buffer from the upper reservoir into the hollow swab shaft 10. The buffer preferably contains a substrate. When the buffer enters the hollow swab shaft 10, it preferably elutes the wound fluid sample from the swab 15. When the reaction is complete, preferably after a specified period of time, such as, for example, 5, 10, or 15 minutes, the swab 15 penetrates beyond a foil seal separating the swab 15 from an inhibitor 20 to stop the reaction. The inhibitor 20 is preferably a protease inhibitor.

In a further embodiment, the subject invention provides a kit for wound mapping. In one embodiment, the kit comprises a membrane as described herein and instructions for use of the membrane to map wounds.

By using the assays of the subject invention, the caregiver is able to assess the biological activity present in the actual wound bed. Further, the caregiver is more readily able to see the direct impact of various treatments on the wound. Advantageously, a picture of the wound environment serves as justification for applying more advanced wound management technologies on a case-by-case basis (i.e. advance personalized medicine).

The assays of the subject invention are amenable to a number of readily available technologies for assessment and archiving of the topographical data. For example, chromogenic-luminescence-, or fluorescence-based detection methods may be used in conjunction with digital photography for sensitive, intuitive observation and storage of patient care records. Finally, in addition to describing the topographical distribution of biofilm and/or microbes, the system can be adapted to assess multiple analytes (i.e. protease, etc.), thus providing a more complete assessment of the wound bed.

Upon conducting the simple procedures of the subject invention, the healthcare professional has very important information not only to treat the condition in an as-needed manner, but also to design and justify subsequent and related treatments, as required by the majority of insurance corporations.

The assays of the subject invention can also be used prior to the application of therapy to ensure that the recipient site is conducive to the therapy (e.g. any treatment applied to the site will not be adversely affected by the presence of biofilm or microbes).

In an embodiment that is specifically exemplified herein, the subject invention provides assays that can be used to determine and/or monitor the status of a wound. The assays are quick and easy-to-use. In specific embodiments, the assays can be carried out by, for example, a nurse utilizing either no instrumentation or only minimal instrumentation. In one embodiment, information about the status of a wound can be readily, easily and reliably generated in 30 minutes or less. In a preferred embodiment, the results are obtained in 15 minutes or less. Most preferably, the results are generated in 10 minutes or less.

In a specific embodiment, the assays of the subject invention are utilized to assess the status of chronic wounds. As used herein, reference to "chronic wounds" refers to wounds that after 2 weeks are not healing properly.

Following are examples which illustrate procedures for practicing the invention. These examples should not be construed as limiting.

EXAMPLE 1

Assay Chamber

Figure 1:
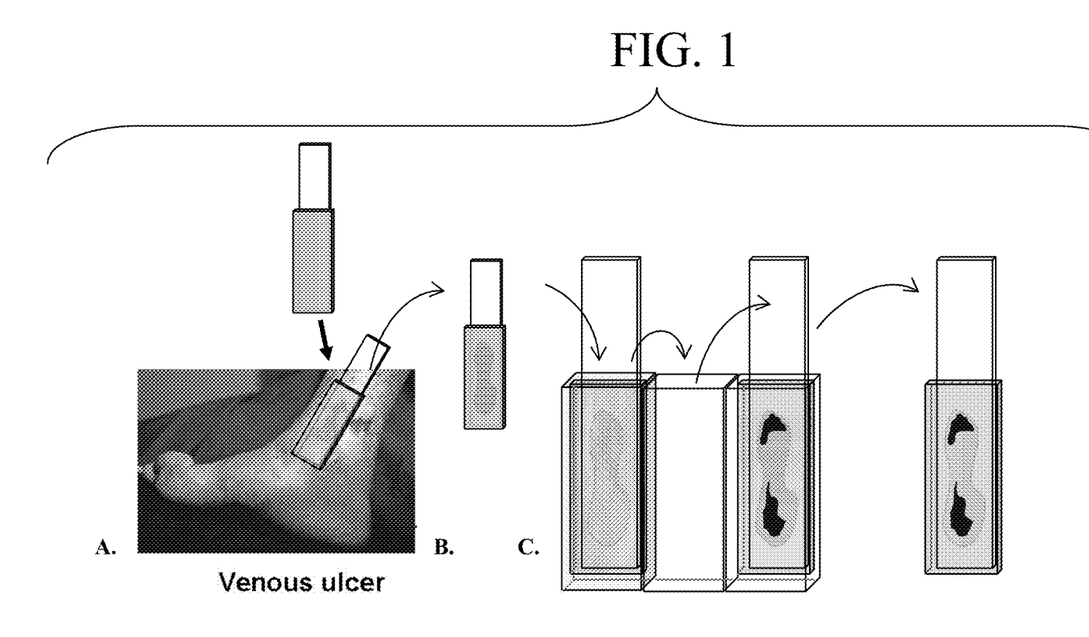
FIG. 1A shows a wound "map" affinity membrane blot that contains the bound ligand (e.g. antibody) being applied to the wound surface.
In FIG. 1B the ligand binds the unique marker for the target microorganism or biofilm (e.g., polysaccharide of biofilm matrix).
FIG. 1C shows the blot is then transferred into a first chamber that contains a solution of the same (or different) ligand that is labeled with a reporter (e.g. alkaline phosphatase enzyme). After a short incubation time (~10 minutes) the wound map blot is transferred into the second chamber to wash out any unbound labeled-ligand and, after rinsing, the blot is transferred into the final chamber that contains the substrate for the enzyme of the labeled-ligand. After a short period of development (~5 minutes) the wound map blot strip is rinsed and the areas of wound surface that contained the microorganism or biofilm are revealed as uniquely "colored" areas.

In one embodiment the subject invention provides an assay chamber for processing a topographical wound map microbial/microbial biofilm detector assay membrane (FIG. 1). An impression is taken of the wound using a membrane for obtaining a specimen of microbial biofilm from wounds (FIG. 1A). The impression can be used to produce copy blots using an appropriate membrane/device, or it can be processed directly. The wash chamber consists of separate chambers containing reaction and wash buffers to process the assay membrane.

EXAMPLE 2

Assay Cassette Method

In one embodiment, the subject invention provides an assay cassette method for processing a topographical wound map membrane. An impression can be taken of the wound using a membrane for obtaining a specimen of microbial biofilm from wounds (FIG. 1A). The impression can be used to produce copy blots using appropriate membrane(s)/device or will be processed directly.

The assay cassette may contain a fluid reservoir at the base containing a compressible material to hold the reaction buffer. The assay cassette may contain an upper dry wicking layer employed to pull fluid through the assay membrane to facilitate the assay reaction and to "wash" the assay membrane.

EXAMPLE 3

Assay Method

FIG. 1 is a schematic of one embodiment of the subject invention. FIG. 1A shows a wound "map" affinity membrane blot that contains the bound ligand (e.g. antibody) to the unique marker of the microorganism (i.e. bacteria, fungi) or biofilm. This membrane is applied to the wound surface. The ligand (e.g. antibody) that is bonded onto the blot binds with the unique marker for the target microorganism or biofilm (e.g., polysaccharide of biofilm matrix). The blot is then transferred into the first chamber of a developing block that contains a solution of the same ligand that is labeled with a reporter (e.g. alkaline phosphatase enzyme). After a short incubation time (~10 minutes) the wound map blot is transferred into the second chamber to wash out any unbound labeled-ligand and after a minute of rinsing the blot is transferred into the final third chamber that contains the substrate for the enzyme of the labeled-ligand.

After a short period of development (~5 minutes) the wound map blot strip is rinsed under running tap water and the areas of wound surface that contained the microorganism or biofilm are revealed as uniquely "colored" areas.

EXAMPLE 4

Alternative Assay Format

In one embodiment, the subject invention provides an assay as follows:
(1) A high capacity binding membrane is used to non-specifically adsorb biological molecules (including, for example, polysaccharides, DNA, proteins and lipids) on a wound. In a preferred embodiment, the membrane is a HYBOND™ nylon sheet.
(2) The membrane is then submerged in a blocking agent. The blocking agent may be, for example, serum albumin or casein. The blocking agent coats any remaining binding sites on the membrane.
(3) The membrane is then briefly submerged in (or sprayed with) a concentrated solution comprising a cationic dye. The membrane may be contacted with the dye(s) for, for example, 1 to 5 minutes, and preferably for about 2-3 minutes. In specific embodiment the dyes may be alcian blue and/or ruthenium red.
(4) The membrane is then rinsed in a solution of salt and dilute acid, with a small amount of methanol or ethanol. In a specific embodiment, the salt solution can be around 0.9% sodium chloride, the acid may be acetic acid (or other acid of similar strength) and the alcohol can be around 1-2%.
(5) The final step is to dry the membrane and observe the dye-stained area that corresponds to the area of the wound bed surface that contains a biofilm.

EXAMPLE 5

Assessment of Biofilm Detection: Polyanionic Exopolysaccharides

Polyanionic exopolysaccharides found in biofilm exopolymeric matrix were assessed. Preferably, a membrane having a high positive charge (such as positively charged nylon or activated papers) is used as the target capture membrane. In contrast to nitrocellulose membranes and uncharged membranes that have negative charges or no charges, respectively, high positively charged membranes are able to tightly bind to the highly negatively charged polysaccharides and bacterial DNA that make up a majority of exopolymeric material of biofilm. See Table 1 below. In one embodiment, Amersham HYBOND™-N+ (GE Healthcare), a cationic nylon membrane, was chosen as the target capture membrane.

TABLE 1

Properties of Materials used for Immobilization of Nucleic Acids

|  | Nitrocellulose | Supported nitrocellulose | Uncharged nylon | Positively charged nylon | Activated papers |
|---|---|---|---|---|---|
| Application | ssDNA, RNA, protein | ssDNA, RNA, protein | ssDNA, dsDNA, RNA, protein | ssDNA, dsDNA, RNA, protein | ssDNA, RNA |
| Binding capacity (μg nucleic acid/cm$^2$) | 80-100 | 80-100 | 400-600 | 400-600 | 2-40 |
| Tensile strength | Poor | Good | Good | Good | Good |
| Mode of nucleic acid attachment[a] | Noncovalent | Noncovalent | Covalent | Covalent | Covalent |
| Lower size limit for efficient nucleic acid retention | 500 nt | 500 nt | 50 nt or bp | 50 nt or bp | 5 nt |
| Suitability for reprobing | Poor (fragile) | Poor (loss of signal) | Good | Good | Good |
| Commercial examples | Schleicher & Schuell BA83,BA85; AMERSHAM ™ HYBOND ™-C; PALL Biodyne A | Schleicher & Schuell BA-S; AMERSHAM ™ HYBOND ™-C extra | AMERSHAM ™ HYBOND ™-N; Stratagene Duralon-UV; DU Pont NEN GeneScreen | Schleicher & Schuell Nytran; AMERSHAM ™ HYBOND ™-N+; Bio-Rad ZetaProbe; PALL Biodyne B; Du Pont NEN GeneScreen Plus | Schleicher & Schuell APT papers |

[a] After suitable immobilization procedure.

Figures 2A, 2B, 2C, 2D, 2E, 2F, 2G, 2H:
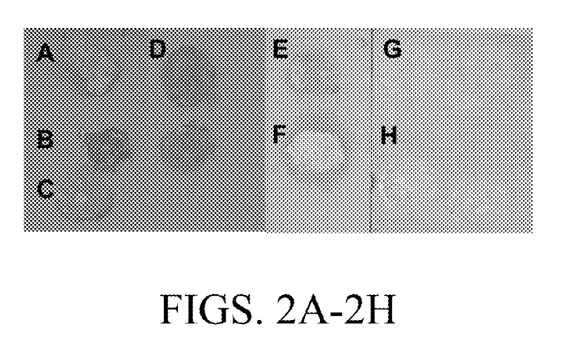
Figures 3A, 3B, 3C, 3D, 3E, 3F:
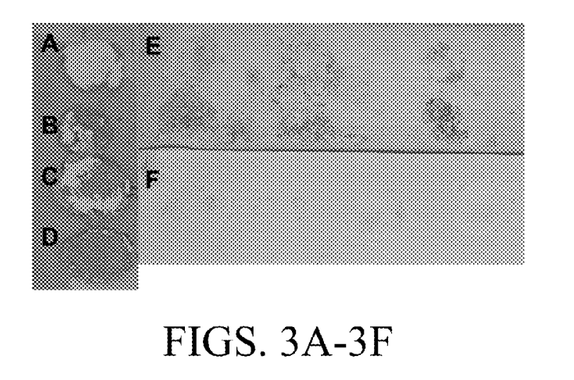

Two cationic chromogenic dyes were chosen as detectors: Alcian Blue 8GX (FIG. 2) and Ruthenium Red (Sigma-Aldrich) (FIG. 3). Early immature 1 and mature 3 day *P. aeruginosa* PAO1 biofilm were cultured using a porcine skin explant biofilm model.

The in vitro biofilm porcine skin explant model includes obtaining fresh pigskin, processing the skin by mechanical depilation, removal of excess fat below the epidermis, and mechanically creating 8 mm explants with 2 mm borehole partial thickness "wound beds." The explants were washed with 10% bleach solution, sterilized 45 minutes with chlorine gas, and washed with sterile PBS.

Explant "wound beds" were inoculated with 10 ul of Log phase bacterial culture of clinically relevant bacterial species (e.g., *Pseudomonas aeruginosa, Staphylococcus aureus*, etc.). The explants were then placed on soft 0.5% soft agar media containing appropriate antibiotics (to which the bacteria in planktonic form are not resistant) to prevent penetration of bacterial biofilm through the bottom of the explant. The bacteria were cultured for 3 to 5 days, with daily transfer to fresh media, to produce mature bacteria biofilm. The explants were treated overnight in liquid media containing 100 MIC of appropriate antibiotic to kill remaining planktonic bacteria, gently washed with sterile PBS, and used as desired (e.g., to assess antimicrobial efficacy of various treatments on immature and mature bacterial biofilm; as a pseudo biofilm infected chronic wound). In certain experiments, explants may then be sonicated in PBS with 5 ul/ml Tween-80 in order to obtain bacterial suspensions for spread plate analysis to determine relative CFU/ml. The explant or the sonicant bacterial suspension may also be assessed using microscopy.

Unsterilized explants and explants in which PAO1 was grown were blotted, from both sides of the explant, onto the membrane. The blots were stained with 5 mg/ml of Alcian Blue (FIG. 2) or Ruthenium Red (FIG. 3) for 1 minute, and washed three times with phosphate buffered saline (PBS) for 30 minutes each. The results showed that, compared to the unsterilized skin control, both dyes can detect PAO1 biofilm using this membrane (FIGS. 2 and 3).

Figures 5A, 5B, 5C:
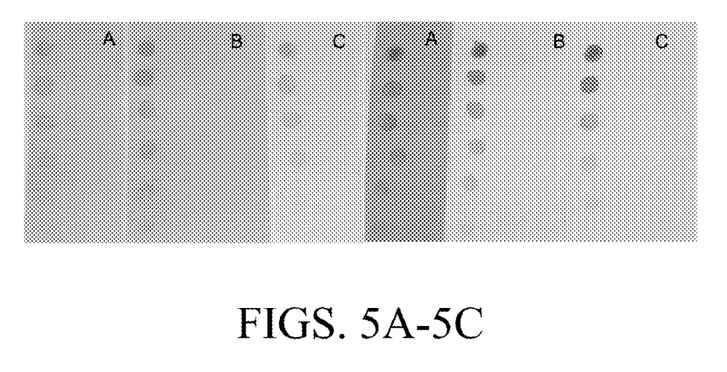
Figure 6A:
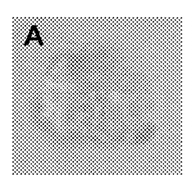
Figure 6B:
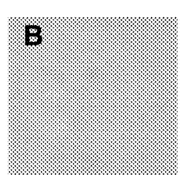
Figure 6C:
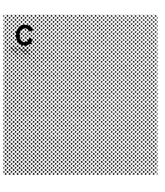
Figure 6D:
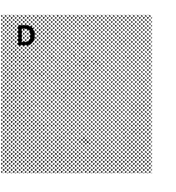
Figure 7:
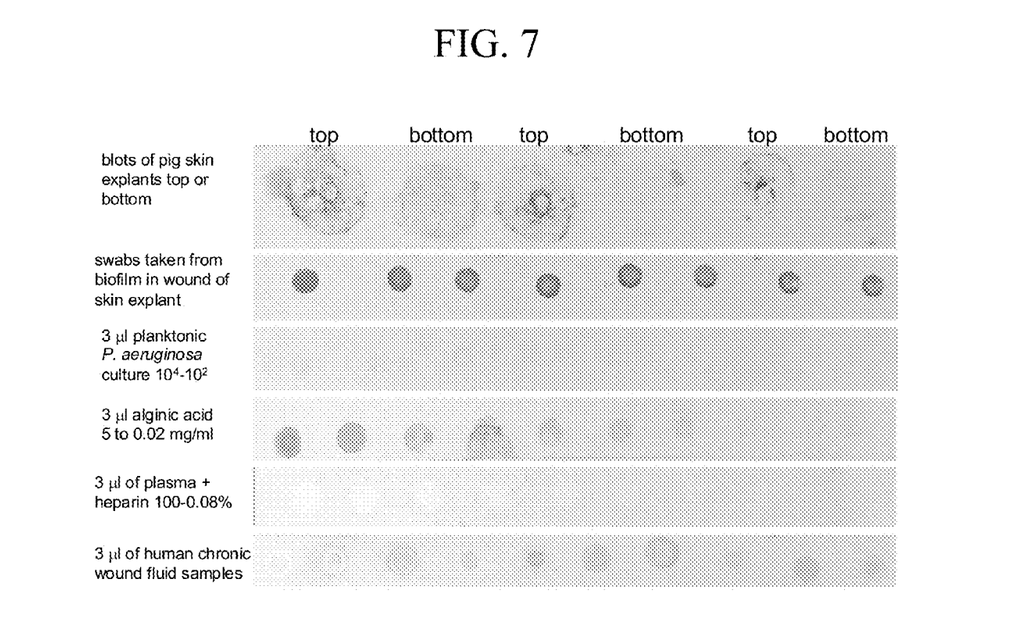
FIG. 7 illustrates colorimetric detection of *Pseudomonas aeruginosa* PAO1 biofilm extracellular polysaccharides (EPS) matrix.
Figure 8A:
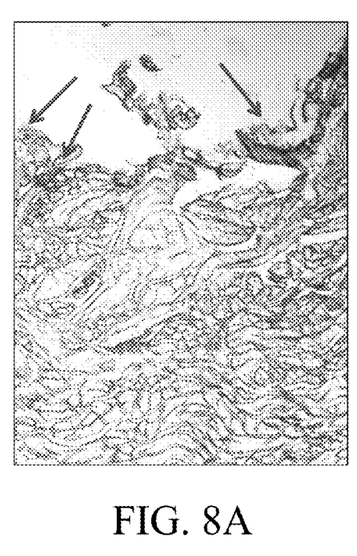
Figure 8B:
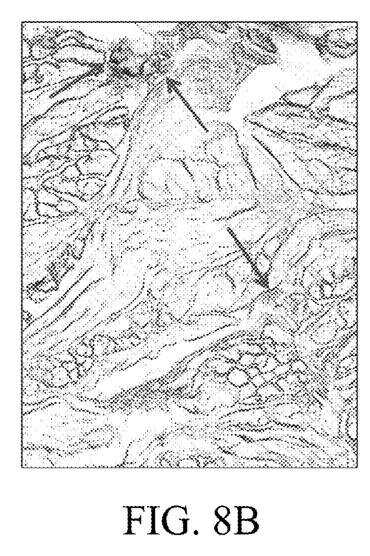
Figure 9:
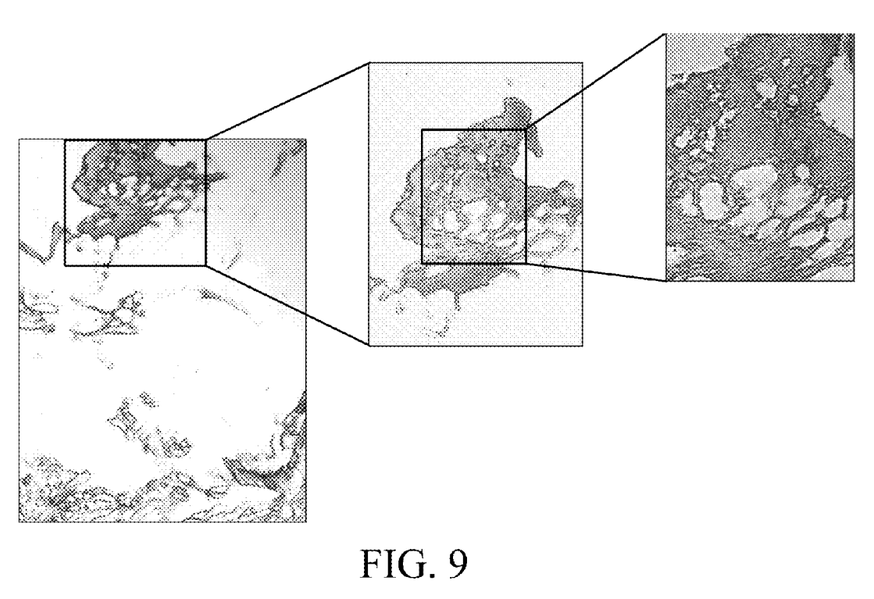
FIG. 9 illustrates microscopic cryosections of dye staining *Pseudomonas aeruginosa* biofilms on pig skin.
Figure 10:
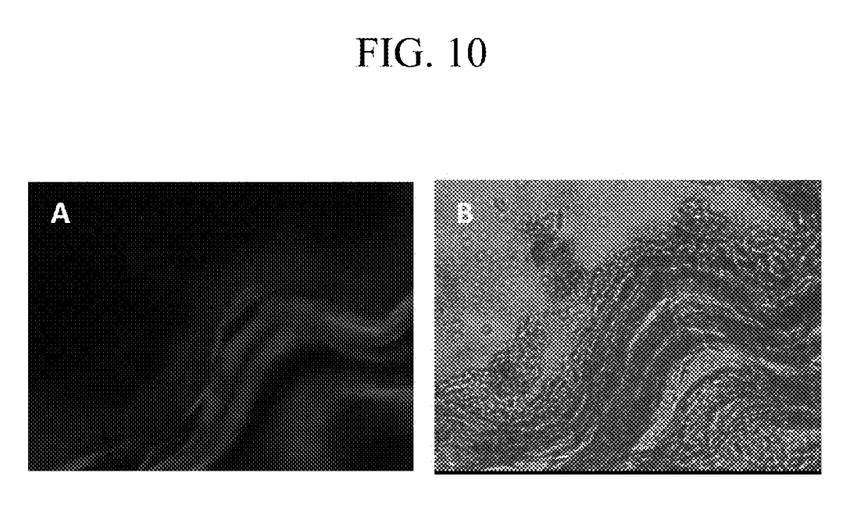
Figure 11:
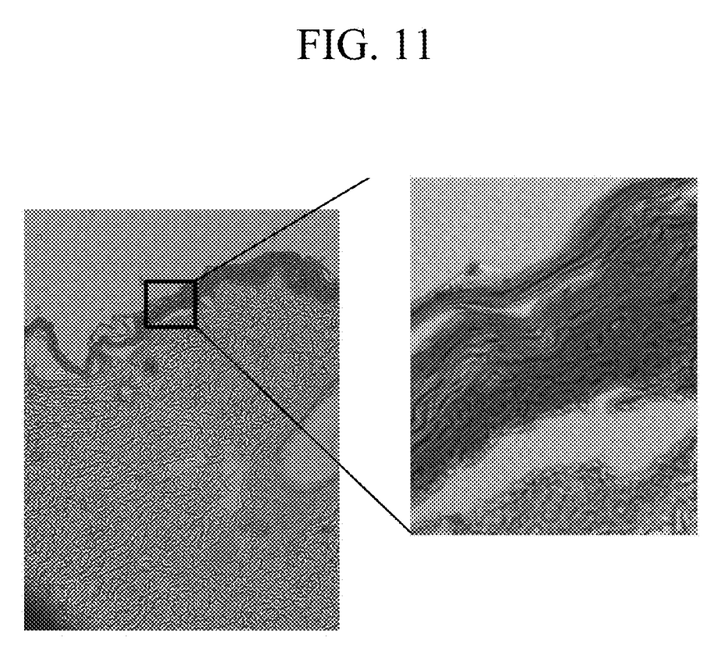
FIG. 11 illustrates bright field microscopic images of paraffin sections of dye staining Psuedomonas aeruginosa biofilms on pig skin. Ruthenium Red 0.1%-0.5% gluteraldehyde in 100 mM cacodylate buffer was prepared by adding 0.03 g ruthenium red and 0.16 mL gluteraldehyde to cacodylate buffer and bringing to 30 mL with buffer. Cacodylate buffer (100 mM) was prepared by adding 4.2782 g cacodylic acid to 200 mL dlH$_2$O. Slides were deparaffinized. Ruthenium red solution was added for one hour. Slide was rinsed with cacodylate buffer for two minutes.
Figure 12:
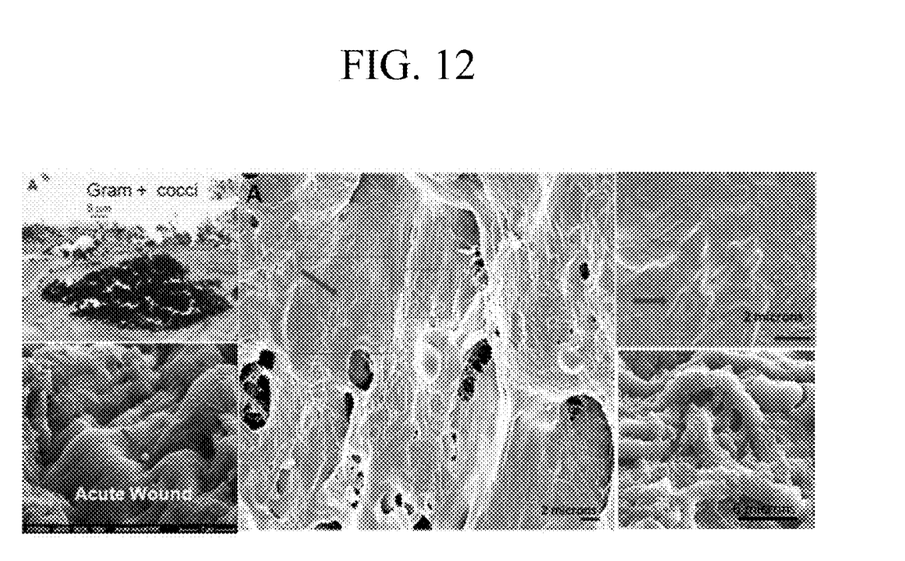

Due to the high background, alternative wash solutions were tested: PBS with 5 ul/ml Tween-80; PBS with 0.1% SDS; 40% methanol with 10% acetic acid. Alginate is the primary polyanionic exopolysaccharide secreted by PAO1 and is the major component of its biofilm matrix. A solution of 5 mg/ml Alginic acid (Sigma-Aldrich) was 2-fold serially diluted and 2 μl of each dilution was dotted onto cationic nylon membrane, stained with 5 mg/ml of Alcian Blue or Ruthenium Red for 1 minute, and washed three times 30 minutes each with one of the wash solutions. The result show that PBS alone (FIGS. 2 and 3) or with 0.1% SDS (FIG. 5A) had high background, PBS with 5 ul/ml Tween-80 had reduced Ruthenium red but not Alcian blue background (FIG. 5B). and 40% methanol with 10% acetic acid solution removed most of the background for both dyes (FIG. 5C). Ruthenium red precipitated during staining of the explant with biofilm blots causing uneven and discolored staining, particularly for the 3 day biofilm blots (FIG. 3), which was resolved before staining the unsterile skin blots (FIG. 3G) as well as the dot blots (FIG. 5).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of mapping the spatial distribution of one or more markers associated with microorganism(s) and/or biofilm(s) in a wound comprising:
    (a) contacting an unstained membrane with the wound, wherein the membrane is positively charged and adsorbs negatively charged biological molecules when contacted with the wound;
    (b) blocking the membrane;
    (c) applying a stain to the blocked membrane and adsorbed biological molecules;
    (d) rinsing the membrane; and
    (e) analyzing the dye stained membrane to determine the spatial distribution of said markers of microorganism(s) and/or biofilm(s) of interest in the wound:
    wherein the stain targets one or more markers associated with microorganism(s) and/or biofilm(s) interest in the wound, wherein the stain comprises a plurality of detection ligand molecules that are specific to one or more negatively charged components found in extracellular matrix of the microbial biofilm produced by certain microbial class(es), genera, and/or species, and wherein at least one of said plurality of detection ligand molecules is targeted to one or more of polyanionic bacterial exopolysaccharide, poly-β-(1-6)-N-acetyl-D-glucosamine, or alginic acid.

2. The method, according to claim 1, wherein the membrane is a nylon membrane.

3. The method, according to claim 1, wherein the method is completed in 30 minutes or less.

4. The method, according to claim 1, wherein the applied stain is alcian blue and/or ruthenium red.

* * * * *